United States Patent [19]

Parekh et al.

[11] Patent Number: 5,760,198
[45] Date of Patent: Jun. 2, 1998

[54] PROCESS FOR PREPARATION OF 4"-DEOXYERYTHROMYCINS A AND B

[75] Inventors: Shyamal L. Parekh, Gurnee; Alexandra E. Graham, Mundelein; Michael John Dipierro, Gurnee; Albert V. Thomas, Vernon Hills, all of Ill.; David A. Riley, Kenosha, Wis.

[73] Assignee: Abbott Laboratories, Abbott Park, Ill.

[21] Appl. No.: 785,451

[22] Filed: Jan. 17, 1997

[51] Int. Cl.$^6$ .................................................. C07H 1/00
[52] U.S. Cl. ........................................ 536/7.2; 536/18.5
[58] Field of Search .............................. 536/7.2, 18.5, 536/18.6, 7.9

[56] References Cited

FOREIGN PATENT DOCUMENTS 9313780  7/1993  WIPO.

OTHER PUBLICATIONS

Sato, T., et al., "Practical Radical Deoxygenation Of Erythromycins By Barton Reaction", *Heterocycles*, vol. 42, No. 2, 1996, pp. 499–502.

*Primary Examiner*—Elli Peselev
*Attorney, Agent, or Firm*—Mona Anand

[57] ABSTRACT

A process for the preparation of 4"-deoxyerythromycins, having the formula:

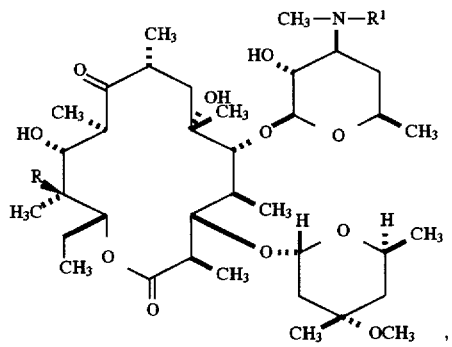

wherein R is H or OH, and $R^1$ is H or loweralkyl by treatment of the 2'-O-acetyl-4"-imidazolylthionocarbonyl-erythromycin starting material with the radical initiator 4,4'-azobis-(4-cyanovaleric acid), $H_3PO_2$ and an organic base in a water-miscible solvent and optionally eliminating the 2'-O-acetyl group. In a preferred embodiment, the water-miscible solvent is an alcohol and the deoxygenation and deacetylation is carried out in one step.

17 Claims, No Drawings

PROCESS FOR PREPARATION OF 4"-DEOXYERYTHROMYCINS A AND B

TECHNICAL FIELD

The present invention relates to a process for the preparation of 4"-deoxy-erythromycins A and B, which have use as intermediates in the preparation of gastrointestinal prokinetic agents.

BACKGROUND OF THE INVENTION

Erythromycins A through D, represented by formula (E),

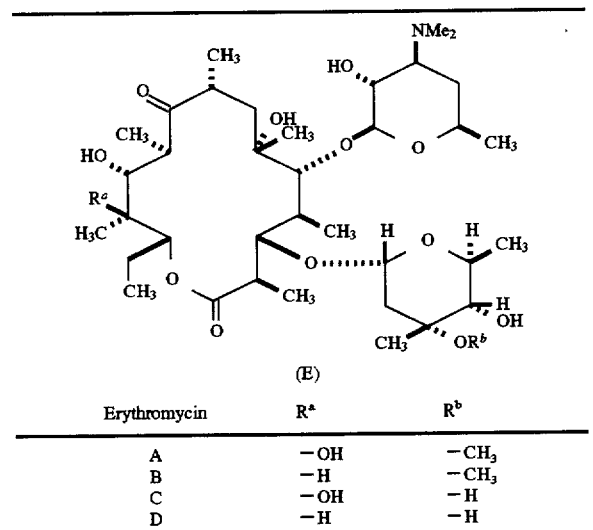

(E)

| Erythromycin | $R^a$ | $R^b$ |
|---|---|---|
| A | —OH | —CH$_3$ |
| B | —H | —CH$_3$ |
| C | —OH | —H |
| D | —H | —H | are well-known and potent antibacterial agents, used widely to treat and prevent bacterial infections.

A recently developed erythromycin derivative having the formula:

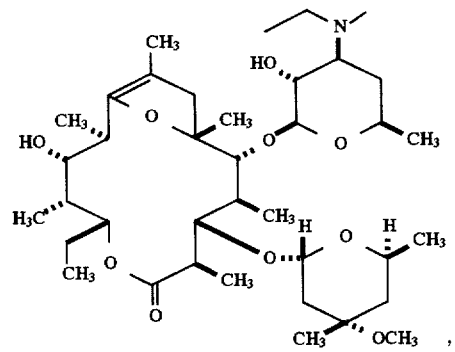

has been described as a prokinetic agent having use in the treatment of gastrointestinal motility disorders (P. A. Lartey, et al., *J. Med. Chem.*, 38 (1793–1798 (1995); R. Faghih, et al., PCT application WO 9313780, published Jul. 22, 1993). The preparation of the above compound requires the preparation of the intermediate compound, namely, 4"-deoxyerythromycin B.

In the process for the deoxygenation of erythromycins, the 4"-hydroxyl group is initially derivatized as a thionocarbonate. This requires prior protection of the more reactive 2'-hydroxyl group as the acetate. Consequently, the intermediate deoxygenated product is a 2'-O-acetate. Deoxygenation at the 4"-position of erythromycin with the aid of azobis(isobutyronitrile (AIBN) has been reported by T. Sato, et al., *Heterocycles*, 42:499 (1996).

An improved and more efficient method of preparation of the 4"-deoxygenated erythromycin compounds would ensure more efficient synthesis and wider availability of the desired prokinetic agents.

SUMMARY OF THE INVENTION

The present invention describes an efficient process for the preparation of 4"-deoxy-erythromycins A and B, which have utility as intermediates in the preparation of prokinetic erythromycin agents, such as that described by Lartey (op. cit.) and its erythromycin A analog. Treatment of the starting materials, 2'-O-acetyl-4"-imidazolylthionocarbonyl-erythromycins A and B, with the radical initiator 4,4'-azobis-(4-cyanovaleric acid) (ACVA) and hypophosphorous acid in a water miscible solvent effects the 4"-deoxygenation and subsequent removal of the 2'-O-acetate affords the desired products in high yields. In a preferred embodiment, the treatment of the starting materials, 2'-O-acetyl-4"-imidazolyl-thionocarbonyl-erythromycins A and B, with the radical initiator ACVA and hypophosphorous acid in an ethanolic solution effects both the 4"-deoxygenation and removal of the 2'-O-acetate and affords the desired products in high yields. The inventive process offers significant safety and reagent removal advantages over the Lartey, et al. process cited above, which utilizes a tin reagent.

In one aspect of the present invention is a process for the preparation of 4"-deoxyerythromycins having the formula:

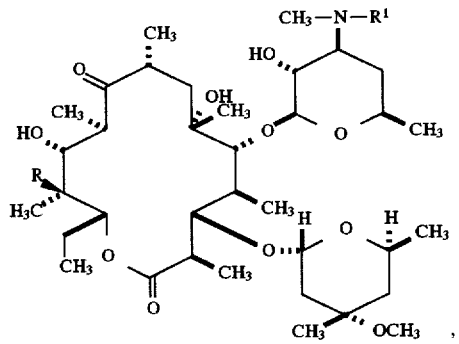

wherein R is H or OH, and $R^1$ is H or loweralkyl; the method comprising:

(a) treating a solution in a water miscible solvent, of a compound having the formula:

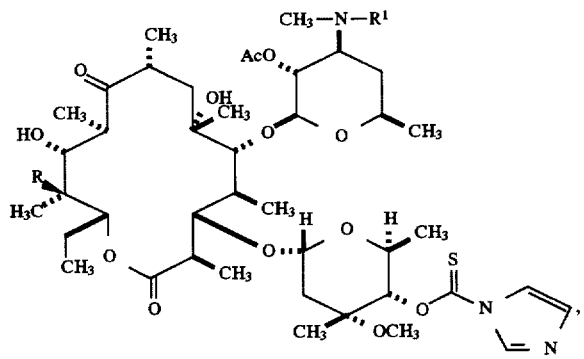

wherein R is H or OH, and $R^1$ is H or loweralkyl, with H$_3$PO$_2$, organic base and 4,4'-azobis-(4-cyanovaleric acid); and b) optionally deacetylating the 2'-acetyl group.

In another aspect, the present invention relates to a process for the preparation of a compound having the formula:

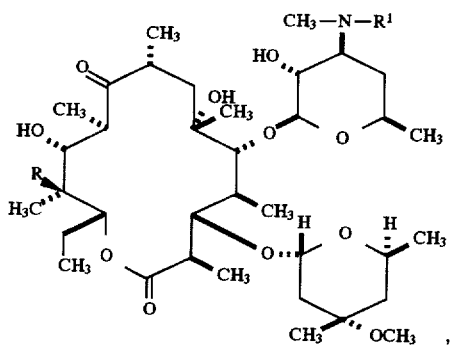

wherein R is H or OH, and R¹ is H or loweralkyl; the method comprising:

(a) treating an alcoholic solution of a compound having the formula:

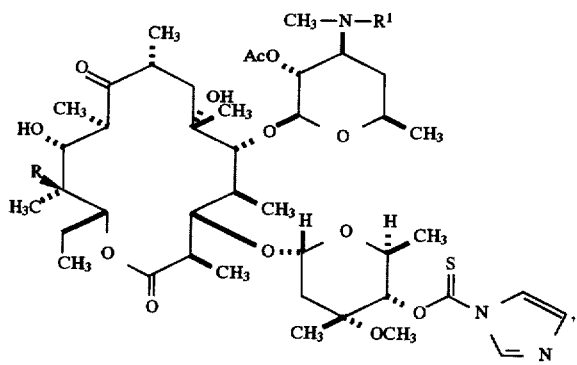

wherein R is H or OH, and R¹ is H or loweralkyl, with $H_3PO_2$, and an organic base and 4,4'-azobis-(4-cyanovaleric acid).

DETAILED DESCRIPTION OF THE INVENTION

The term "loweralkyl" is used herein to refer to alkyl radicals having from 1 to 6 carbon atoms. Examples of loweralkyl groups include methyl, ethyl, propyl, iso-propyl, butyl, t-butyl, pentyl, hexyl, and the like.

In the process of the invention, a solution of the starting compound in step (a) above, in a water miscible solvent, other than an alcohol, is treated with $H_3PO_2$, an organic base and ACVA to afford a 2'-O-acetyl 4"-deoxyerythromycin derivative which is then deacetylated by methods known in the art to give 4"-deoxyerythromycin derivative. In a preferred embodiment, an alcoholic solution of the starting compound in step (a) is treated with $H_3PO_2$, an organic base and ACVA to afford the desired 4"-deoxyerythromycin derivative in one step.

Examples of water miscible solvents that may be used in the process include dioxane, acetonitrile, triglyme, methanol, ethanol, iso-propanol, or a mixture thereof. In a preferred embodiment, each solvent may be used independently, one solvent, preferably ethanol, may be used at the beginning of the reaction and another, preferably methanol, added in the later stages of the reaction.

The reaction is typically carried out at reflux temperature, i.e., between about 60° C. to about 95° C. The reaction in the alcoholic solution is generally carried out at a temperature of from about 60° C. to about 82° C.

The organic base used may be triethylamine, N-ethylpiperidine, N-methylpiperidine, or pyridine. The reaction can also be carried out with a salt of hypophosphorous acid and N-ethylpiperidine, namely, N-ethylpiperidine hypophosphite. The amounts of hypophosphorous acid and the base, or N-ethylpiperidine hypophosphite, utilized may be independently between 10 to 20 equivalents (relative to 1 equivalent of starting material), and the ACVA utilized may be between 0.1 and 1.0 equivalents, based upon 1 equivalent of the starting compound. The reaction may be carried out with the optional presence of an additional base such as $NaHCO_3$ or $K_2CO_3$, which may be present in amounts from about 0 to 1.0 equivalents. The time required for complete utilization of the starting material may vary depending upon the particular combination of solvents, concentrations, timing of addition of the reagents and temperature and typically is from about 1 to about 24 hours, but preferably about 4 to about 12 hours.

4,4'-Azobis-(4-cyanovaleric acid) possesses advantages over other radical initiators such as azobis(isobutyronitrile) (AIBN) and azobis(cyclohexanecarbonitrile) (ACCN) in that it is water soluble and also that the radical initiated reaction may be performed at lower temperatures. The water solubility of the initiator is of particular advantage, as this property allows the initiator to be separated from the water insoluble 4"-deoxygenated product by partitioning with aqueous base. The alcoholic solvents employed in the process also have the advantages of water solubility, low toxicity and easy removal from the product.

Other water soluble free radical initiators that can be used are 2,2'-azobis[2-(imidazolin-2-yl)propane]dihydrochloride (AIBP) and 2,2-azobis(amidinopropane) -dihydrochloride (ABAP). These initiators can be dissolved in other water miscible solvents such as dioxane, acetonitrile, triglyme and the like. However, the percent conversion and the yields of the isolated product are not as desirable as those obtained with ACVA.

In one embodiment of the process of the invention, R in the starting compound is H. In another embodiment of the process of the invention, R in the starting compound is OH.

In a preferred embodiment of the invention, the solvent is methanol, ethanol or iso-propanol, and from 0.1 to 1.0 equivalents of ACVA, 10 to 20 equivalents of $H_3PO_2$ and 10 to 20 equivalents of triethylamine are reacted with 1 equivalent of starting material.

In a more preferred embodiment of the process, 0.5–0.8 equivalents of ACVA, 10 equivalents of $H_3PO_2$ and 20 equivalents of triethylamine are reacted with 1 equivalent of starting material with a combination of ethanol and methanol as solvents. The ethanol and methanol may be used as a mixture, normally about 80 parts of ethanol to about 20 parts of methanol, or they may be utilized in sequence, with ethanol as the first solvent and with methanol added later in the reaction.

EXPERIMENTAL

The following Examples are presented for the purpose of illustrating, but not limiting, the processes of the invention. The starting material of Examples 1–10 below, namely 2'-O-acetyl-4"-imidazolylthionocarbonyl-erythromycin B, was prepared according to PCT application WO 9313780, the relevant portions of which are incorporated herein by reference. The erythromycin A analog, used in Examples 11 and 12, was prepared by substituting erythromycin A for erythromycin B in that procedure.

EXAMPLES 1–10

Preparation of 4"-deoxyerythromycin B

Example 1

1 equivalent of ACVA (28 g, 0.1 mol.) available from Wako Chemicals, Inc., was added, under nitrogen, to a solution of 2'-O-acetyl-4"-imidazolylthionocarbonyl-erythromycin B (87 g, 0.1 mole) in ethanol (1.4 L). The solution, on refluxing, was treated with a mixture of 13 equivalents of triethylamine (132 g, 1.3 mol) and 10 equivalents of 50% aqueous hypophosphorous acid (132 g, 1 mol) in ethanol (0.34 L). The reaction mixture was heated at reflux for 1–1.5 hours. Ethanol was then removed under vacuum, and methanol added. The mixture was heated at reflux temperature for 4–6 hours. The volatile alcohols were removed under vacuum, and the residue was extracted with ethyl acetate. The extract was washed with aqueous 10% $NaHCO_3$, water, dried ($MgSO_4$) and concentrated (70% yield).

Example 2

0.5 equivalent of ACVA (14 g, 0.05 mol was added, under nitrogen, to a solution of 2'-O-acetyl-4"-imidazolylthionocarbonyl-erythromycin B (87 g, 0.1 mole) in ethanol (1.4 L). The solution, on refluxing, was treated with a mixture of 20 equivalents of triethylamine (202 g, 2 mol) and 10 equivalents of 50% aqueous hypophosphorous acid (132 g, 1 mol) in ethanol ( 0.34 L). The reaction mixture was heated at reflux for 1–1.5 hours. Ethanol was then removed under vacuum, and methanol added. The mixture was heated at reflux temperature for 4–6 hours. The volatile alcohols were removed under vacuum, and the residue was extracted with ethyl acetate. The extract was washed with aqueous 10% $NaHCO_3$, water, dried ($MgSO_4$) and concentrated (88% yield).

Example 3

A solution of 2'-O-acetyl-4"-imidazolylthionocarbonyl-erythromycin B (87 g, 0.1 mole) in ethanol (1.4 L) was heated at 65° C. for 18 to 20 hours. 0.5 equivalents of ACVA (14 g, 0.05 mol) was added, under nitrogen, and the solution heated to reflux then treated with a mixture of 20 equivalents of triethylamine (202 g, 2 mol) and 10 equivalents of 50% aqueous hypophosphorous acid (132 g, 1 mol) in ethanol ( 0.34 L). The reaction was heated at reflux for 1–1.5 hours. Ethanol was removed under vacuum, and the residue was extracted with ethyl acetate. The extract was washed with aqueous 10% $NaHCO_3$, water, dried ($MgSO_4$) and concentrated (65% yield).

Example 4

0.5 equivalents of ACVA (14 g, 0.05 mol) was added, under nitrogen, to a solution of 2'-O-acetyl-4"-imidazolylthionocarbonyl-erythromycin B (87 g, 0.1 mole) in ethanol (1.4 L). The solution, on refluxing, was treated with a mixture of 13 equivalents of triethylamine (132 g, 1.3 mol) and 10 equivalents of 50% aqueous hypophosphorous acid (132 g, 1 mol) in ethanol (0.34 L). The reaction mixture was heated at reflux for 1–1.5 hours. Ethanol was condensed under vacuum to ⅓ volume and methanol (0.5 L) added. The mixture was heated at 45° C. for 10–15 hours. The volatile alcohols were removed under vacuum, and the residue was extracted with ethyl acetate. The extract was washed with aqueous 10% $NaHCO_3$, water, dried ($MgSO_4$) and concentrated (85% yield).

Example 5

0.5 equivalents of ACVA (14 g, 0.05 mol) was added, under nitrogen, to a solution of 2'-O-acetyl-4"-imidazolylthionocarbonyl-erythromycin B (87 g, 0.1 mole) in ethanol (1.4 L). The solution, on refluxing, was treated with 0.5 equivalents of potassium carbonate (6.9 g, 0.05 mol) and a mixture of 15 equivalents of triethylamine (152 g, 1.5 mol) and 10 equivalents of 50% aqueous hypophosphorous acid (132 g, 1 mol) in ethanol (0.34 L). The reaction mixture was heated at reflux for 18–22 hours. Ethanol was removed under vacuum, and the residue was extracted with ethyl acetate. The extract was washed with aqueous 10% $NaHCO_3$, water, dried ($MgSO_4$) and concentrated (88% yield).

Example 6

0.5 equivalents of ACVA (14 g, 0.05 mol) was added, under nitrogen, to a solution of 2'-O-acetyl-4"-imidazolylthionocarbonyl-erythromycin B (87 g, 0.1 mole) in ethanol (1.4 L). The solution, on refluxing, was treated with 0.5 equivalent of sodium bicarbonate (4.2 g, 0.05 mol) and a mixture of 15 equivalents of triethylamine (152 g, 1.5 mol) and 10 equivalents of 50% aqueous hypophosphorous acid (132 g, 1 mol) in ethanol (0.34 L). The reaction mixture was heated at reflux for 18–22 hours. Ethanol was removed under vacuum, and the residue was extracted with ethyl acetate. The extract was washed with aqueous 10% $NaHCO_3$, water, dried ($MgSO_4$) and concentrated (79% yield).

Example 7

0.5 equivalents of ACVA (14 g, 0.05 mol) was added, under nitrogen, to a solution of 2'-O-acetyl-4"-imidazolylthionocarbonyl-erythromycin B (87 g, 0.1 mole) in an ethanol/methanol mixture (80:20, 1.4 L). The solution, on refluxing, was treated with 1 equivalent of sodium bicarbonate (8.4 g, 0.1 mol) and a mixture of 20 equivalents of triethylamine (202 g, 2 mol) and 8 equivalents of 50% aqueous hypophosphorous acid (106 g, 0.8 mol) in an ethanol/methanol mixture (80:20, 0.34 L). The reaction was heated at reflux for 8 hours. The volatile alcohols were removed under vacuum, methanol (500 mL) was added and the solution refluxed for another 1 hour. Methanol was removed under vacuum and the residue was extracted with ethyl acetate. The extract was washed with aqueous 10% $NaHCO_3$, water, dried ($MgSO_4$) and concentrated (63% yield).

Example 8

0.5 equivalents of ACVA (14 g, 0.05 mol) was added, under nitrogen, to a solution of 2'-O-acetyl-4"-imidazolylthionocarbonyl-erythromycin B (87 g, 0.1 mole) in an ethanol/methanol mixture (80:20, 1.4 L). The solution, on refluxing, was treated with 0.5 equivalent of sodium bicarbonate (4.2 g, 0.05 mol) and a mixture of 15 equivalents of triethylamine (152 g, 1.5 mol) and 10 equivalents of 50% aqueous hypophosphorous acid (132 g, 1 mol) in an ethanol/methanol mixture (80:20, 0.34 L). The reaction was heated at reflux for 18–22 hours. The volatile alcohols were removed under vacuum and the residue was extracted with ethyl acetate. The extract was washed with aqueous 10% $NaHCO_3$, water, dried ($MgSO_4$) and concentrated (79% yield).

Example 9

0.5 equivalent of ACVA (14 g, 0.05 mol) was added, under nitrogen, to a solution of 2'-O-acetyl-4"- imidazolylthionocarbonyl-erythromycin B (87 g, 0.1 mole) in an ethanol/methanol mixture (80:20, 0.85 L). The solution, on refluxing, was treated with a mixture of 20 equivalents of triethylamine (202 g, 2 mol) and 10 equivalents of 50% aqueous hypophosphorous acid (132 g, 1 mol) in an ethanol/methanol mixture (80:20, 0.2 L). The reaction was heated at reflux for 10–12 hours. The volatile alcohols were removed under vacuum, and the residue was extracted with ethyl acetate. The extract was washed with aqueous 10% $NaHCO_3$, water, dried ($MgSO_4$) and concentrated (63% yield).

Example 10

0.5 equivalent of ACVA (14 g, 0.05 mol) was added, under nitrogen, to a solution of 2'-O-acetyl-4"-imidazolylthionocarbonyl-erythromycin B (87 g, 0.1 mole) in an ethanol/methanol mixture (80:20, 1.4 L). The solution, on refluxing, was treated with a mixture of 20 equivalents of triethylamine (202 g, 2 mol) and 10 equivalents of 50% aqueous hypophosphorous acid (132 g, 1 mol) in an ethanol/methanol mixture (80:20, 0.34 L). The reaction was heated at reflux for 10–14 hours. The volatile alcohols were removed under vacuum, and the residue was extracted with ethyl acetate. The extract was washed with aqueous 10% $NaHCO_3$, water, dried ($MgSO_4$) and concentrated (90% yield).

Examples 11–12

Examples 11–12 illustrate the preparation of 4"-deoxyerythromycin A.

Example 11

0.8 equivalents of ACVA (11 g, 0.04 mol) was added, under nitrogen, to a solution of 2'-O-acetyl-4"-imidazolylthionocarbonyl-erythromycin A (44 g, 0.05 mole) in an ethanol/methanol mixture (80:20, 0.7 L). The solution, on refluxing, was treated with a mixture of 20 equivalents of triethylamine (101 g, 1 mol) and 10 equivalents of 50% aqueous hypophosphorous acid (66 g, 0.5 mol) in an ethanol/methanol mixture (80:20, 0.2 L). The reaction was heated at reflux for 1 hour and then at 60° C. for 10–14 hours. The volatile alcohols were removed under vacuum, and the residue was extracted with ethyl acetate. The extract was washed with aqueous 10% $NaHCO_3$, water, dried ($MgSO_4$) and concentrated (90% yield).

Example 12

0.5 equivalents of ACVA (7 g, 0.025 mol) was added, under nitrogen, to a solution of 2'-O-acetyl-4"-imidazolylthionocarbonyl-erythromycin A (44 g, 0.05 mole) in ethanol (0.7 L). The solution, on refluxing, was treated with a mixture of 15 equivalents of triethylamine (76 g, 0.75 mol) and 10 equivalents of 50% aqueous hypophosphorous acid (66 g, 0.5 mol) in ethanol (0.2 L). The reaction mixture was heated at reflux for 18–22 hours. Ethanol was removed under vacuum, and the residue was extracted with ethyl acetate. The extract was washed with aqueous 10% $NaHCO_3$, water, dried ($MgSO_4$) and concentrated (43% yield).

Example 13

Example 13 illustrates the preparation of 2'-O-acetyl-4"-deoxyerythromycin B using other water miscible solvents and reaction conditions.

ACVA (1.61 g, 5.75 mmol) was added, under nitrogen, to a solution of 2'-O-acetyl-4"-imidazolylthionocarbonyl-erythromycin B (5 g, 5.75 mmol) in 50 mL of a water miscible solvent or mixture of solvents using the reaction condition as set forth in the Table 1 below. The solution, on heating to the desired temperature, was treated with a mixture of triethylamine (7 g, 69 mmol) and 50% aqueous hypophosphorous acid (7.6 g, 57.5 mmol) in the solvent (25 mL). The reaction mixture was heated for 1–2 hours and quenched with cold brine. The solvent was removed under vacuum, and the residue extracted with ethyl acetate. The extract was washed with aqueous 10% $NaHCO_3$, water, dried over $MgSO_4$ and concentrated.

TABLE 1

| Exp. 13 | Solvent | Base | Temp./ °C. | Time/ Hours | % Yield |
|---|---|---|---|---|---|
| a | Dioxane | N-ethylpiperidine | 92° | 2 | 55 |
| b | Dioxane | Triethylamine | 92° | 2 | 68 |
| c | $CH_3CN:H_2O$ (5:1) | Triethylamine/tetrabutyl ammonium bromide | Reflux | 2 | 50 |
| d | Triglyme | Triethylamine | 92° | 1.5 | 50 |
| e | Triglyme: $CH_3CN$ (1:1) | Triethylamine | 85° | 1.5 | 63 |

What is claimed is:

1. A process for the preparation of 4"-deoxyerythromycins having the formula:

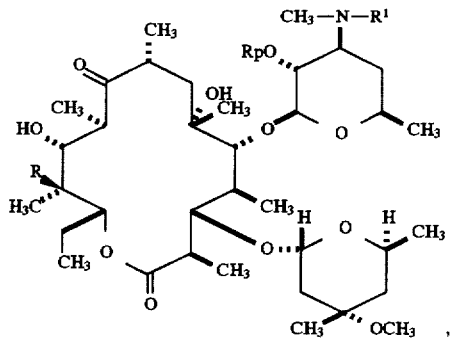

wherein R is H or OH, Rp is H or acetyl, and $R^1$ is H or loweralkyl; the method comprising:

(a) treating a solution in a water miscible solvent other than an alcohol, of a starting material compound having the formula:

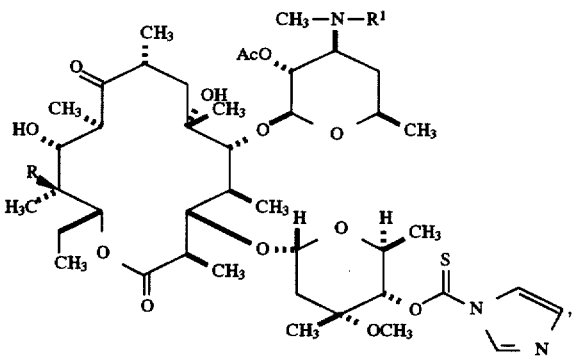

wherein R is H or OH, and $R^1$ is H or loweralkyl, with $H_3PO_2$, an organic base and 4,4'-azobis-(4-cyanovaleric acid); and b) optionally deacetylating the 2'-acetyl group.

2. A process for the preparation of a compound having the formula:

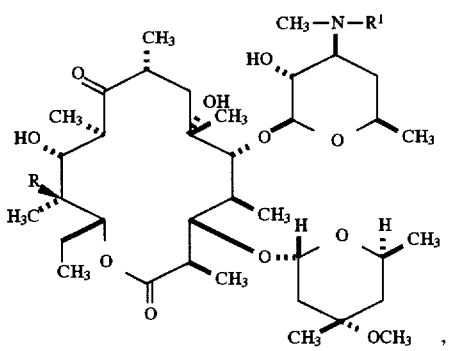

wherein R is H or OH, and $R^1$ is H or loweralkyl; the method comprising:

(a) treating an alcoholic solution of a starting material compound having the formula:

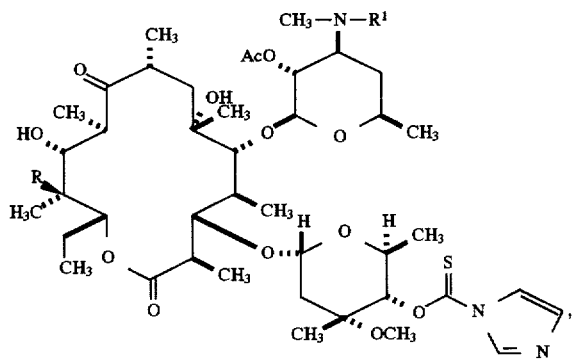

wherein R is H or OH, and $R^1$ is H or loweralkyl, with $H_3PO_2$, organic base and 4,4'-azobis-(4-cyanovaleric acid).

3. The process according to claim 1 wherein R is H.

4. The process according to claim 3, wherein the solvent is dioxane, acetonitrile, triglyme, or a mixture thereof.

5. The process according to claim 2 wherein R is H.

6. The process according to claim 5, wherein the solvent is dioxane, acetonitrile, triglyme, or a mixture thereof.

7. The process according to claim 1, wherein the process is carried out at a temperature from about 60° C. to about 95° C. for a period of from about 1 to about 24 hours.

8. The process according to claim 2, wherein the solvent is methanol, ethanol, iso-propanol, or a mixture thereof, and from 0.1 to 1.0 equivalents of 4,4'-azobis-(4-cyanovaleric acid), 10 to 20 equivalents of $H_3PO_2$ and 10 to 20 equivalents of triethylamine are reacted with 1 equivalent of starting material.

9. The process according to claim 8, wherein 0.5–0.8 equivalents of 4,4'-azobis-(4-cyanovaleric acid), 10 equivalents of $H_3PO_2$ and 20 equivalents of triethylamine are reacted with 1 equivalent of starting material with a mixture of ethanol and methanol.

10. The process according to claim 2, wherein the process is carried out at a temperature from about 60° C. to about 82° C. for a period of from about 1 to about 24 hours.

11. The process according to claim 10, wherein the organic base is triethylamine.

12. The process according to claim 1 wherein R is OH.

13. The process according to claim 2, wherein R is OH.

14. The process according to claim 13, wherein the base is triethylamine.

15. The process according to claim 14, wherein the process is carried out at a temperature from about 60° C. to about 82° C. for a period of from about 1 to about 24 hours.

16. The process according to claim 15, wherein the solvent is methanol, ethanol, iso-propanol, or a mixture thereof and from 0.1 to 1.0 equivalents of 4,4'-azobis-(4-cyanovaleric acid), 10 to 20 equivalents of $H_3PO_2$ and 10 to 20 equivalents of triethylamine are reacted with 1 equivalent of starting material.

17. The process according to claim 16, wherein 0.5–0.8 equivalents of 4,4'-azobis-(4-cyanovaleric acid), 10 equivalents of $H_3PO_2$ and 20 equivalents of triethylamine are reacted with 1 equivalent of starting material with a combination of ethanol and methanol as solvents.

* * * * *